(12) United States Patent
Tereschouk

(10) Patent No.: US 9,283,362 B2
(45) Date of Patent: Mar. 15, 2016

(54) SEMI-RIGID CONCAVE APPLICATOR OF ENCAPSULATED LIQUIDS

(71) Applicant: Misha Tereschouk, Frankfurt (DE)

(72) Inventor: Misha Tereschouk, Frankfurt (DE)

( * ) Notice: Subject to any disclaimer, the term of this patent is extended or adjusted under 35 U.S.C. 154(b) by 86 days.

(21) Appl. No.: 14/348,603

(22) PCT Filed: Mar. 4, 2013

(86) PCT No.: PCT/IB2013/000943
§ 371 (c)(1),
(2) Date: Apr. 14, 2014

(87) PCT Pub. No.: WO2013/132351
PCT Pub. Date: Sep. 12, 2013

(65) Prior Publication Data
US 2014/0234008 A1  Aug. 21, 2014

Related U.S. Application Data

(60) Provisional application No. 61/608,322, filed on Mar. 8, 2012.

(51) Int. Cl.
| | | |
|---|---|---|
| B43K 5/14 | (2006.01) |
| A61M 35/00 | (2006.01) |
| A45D 34/04 | (2006.01) |
| A45D 37/00 | (2006.01) |
| A45D 40/26 | (2006.01) |
| A61F 13/40 | (2006.01) |

(52) U.S. Cl.
CPC ............ *A61M 35/003* (2013.01); *A45D 34/04* (2013.01); *A45D 37/00* (2013.01); *A45D 40/26* (2013.01); *A61M 35/006* (2013.01); *A45D 2200/1045* (2013.01)

(58) Field of Classification Search
CPC .......................... A61M 35/006; A61M 35/003
USPC ................................................ 401/134; 604/3
See application file for complete search history.

(56) References Cited

U.S. PATENT DOCUMENTS

| | | | | |
|---|---|---|---|---|
| 4,596,481 | A * | 6/1986 | Tanaka | A47L 23/05 401/132 |
| 5,704,723 | A * | 1/1998 | Salisian | A47K 7/03 401/201 |
| 6,508,604 | B1 * | 1/2003 | Bechmann | A45D 34/04 222/541.3 |
| 7,419,321 | B2 * | 9/2008 | Tereschouk | A45D 34/04 401/132 |
| 7,604,623 | B2 * | 10/2009 | Brunner | C11D 17/041 604/383 |
| 8,066,444 | B2 * | 11/2011 | Rippl | A47L 13/17 401/133 |
| 8,113,730 | B2 * | 2/2012 | Maloney | A47L 13/17 206/229 |
| 8,157,464 | B2 * | 4/2012 | Prax | A45D 34/04 401/132 |

* cited by examiner

*Primary Examiner* — Jennifer C Chiang

(57) ABSTRACT

A hand applicator of encapsulated liquids for their even distribution on surfaces includes an upper side (an impermeable membrane), a capsule of a liquid, an evenly perforated dissector, and a working side (an absorber) and is characterized in that the dissector is non-collapsible semi-rigid concave and contains the capsule. The upper side includes semi-rigid and outer membranes, and is flat and non-folding. The dissector has elevations on its inside. The impermeable membrane and capsule are permanently fixed together or have a common wall. The capsule is an easily peelable, high-barrier blister and includes an aid for opening at a predetermined location. The upper side, dissector, and working side are welded together along the edge of the applicator resulting in a rounded seam that essentially follows the spherical curvature of the dissector. The semi-rigid membrane has an aperture over the capsule and a cut-through handle with a diametric hinge and stiffeners.

20 Claims, 5 Drawing Sheets

SEMI-RIGID CONCAVE APPLICATOR OF ENCAPSULATED LIQUIDS

BACKGROUND OF THE INVENTION

1. Field of the Invention

The invention relates to cosmetics, personal care, and pharmaceuticals, and more particularly to manual applicators of encapsulated liquids for cosmetic, hygienic, or medical purposes.

2. Description of the Prior Art

U.S. Pat. No. 7,419,321 and EP1679096 (Tereschouk) describe a manual applicator of encapsulated liquids that includes an absorber, a drainable dissector, and a back side with a central duplication serving as a grip that are welded together along the edge of the applicator. A capsule (preferably, pressurized) of a liquid is elastically fixed between the flat flexible back side and dissector. This solution has been found to have the following limitations:

- After a rupture of the capsule, the applicator collapses (flattening of the applicator is mandatory for bringing the grip into the working vertical position), which causes its deformation and loss of stability (the absorber becomes flabby and folding; the risen grip is loose and poorly controllable) and hinders its use;
- The applicator made of flexible materials is unstable and often bends, particularly on curved surfaces; the bent down edge may scratch the skin;
- The welding seam of the applicator often leaks at the back side thickenings (at folds of the flat back side and at the grip welding points);
- Pressurized capsules do not allow sufficient shelf life, occupy much storage space, and may spontaneously rupture while non-pressurized capsules are hard to break in the hand;
- The weight of capsules is spread over few central elevations (knobs) of the flat dissector, which results in an uneven stretching of the capsule bottom and its propensity to a spontaneous rupture.

Though Tereschouk identified the problem of the applicator warping in use and indicated that this could be solved by making the flat dissector or the back side or both of them more rigid, no other aforementioned problems were identified.

Accordingly, an object of this invention was to create an applicator of encapsulated liquids that would not collapse, leak, or scratch, and has a sufficient shelf life and smaller dimensions for the same liquid volume. Another object was to find a solution that would make the applicator more rigid (unbending) and functioning on curved surfaces.

SUMMARY OF THE INVENTION

The invention is a hand applicator of encapsulated liquids for their even distribution on surfaces that includes an upper side (an impermeable membrane), a capsule of a liquid, an evenly perforated dissector, and a working side (an absorber). The upper side, dissector, and working side are fixed (welded) together along the edge of the applicator. A slight manual compression of the applicator causes the capsule to open and release the liquid that flows through the dissector perforations and evenly infuses the absorber.

To meet the objects of an applicator that does not collapse and lose stability after the capsule has opened and flattened, and which does not deform, bend, leak, or scratch, the dissector of this invention is semi-rigid concave and provides with a secure and essentially matching space to contain the entire capsule. The dissector protects the capsule against a spontaneous rupture in handling, storage, and transportation. The semi-spherical shape of the dissector determines the semi-spherical shape of the applicator working side composed of a soft absorber and ensures a smooth glide over and an even application of the liquid on a variety of surfaces, particularly curved.

The flat upper side may include flat adjacent membranes: a semi-rigid membrane outside the impermeable membrane, and an outer membrane outside the semi-rigid membrane. The upper side extends without folding over the dissector, which contains the entire capsule. This ensures uniform thickness and seal strength of the applicator seam.

The semi-rigid membrane contributes to the stability of the applicator created primarily by the semi-rigid dissector, and provides with stable structure and support for the applicator handle. The semi-rigid membrane includes a semi-circular cut-through portion forming a handle that rises as a lever around a hinge at the handle base upon a manual pressure on the capsule through the fixed portion of the semi-rigid membrane. For a better balance, the hinge is located preferably at the diameter of the applicator. The handle may include stiffeners for its greater stability during an application. The semi-rigid membrane and handle with stiffeners can be produced by thermoplastic molding or thermoforming. The semi-rigid membrane may include an aperture in its fixed portion over the capsule for the user's finger to press directly on the capsule and ease its opening.

The outer membrane serves mainly esthetical, hygienic, and printing purposes.

In a preferred embodiment, the evenly perforated dissector also includes evenly spread elevations on the inside (a drainable dissector). An unobstructed draining space is created between the elevations for the released liquid to freely reach the perforations. The dissector can be produced by thermoforming or molding. In another embodiment, the impermeable membrane and capsule are permanently fixed together or have a common wall, so that the capsule is immobilized in the dissector cavity without touching the perforations. This obviates the need for the dissector elevations as a measure to forestall the blockage of the perforations by an opened capsule.

A capsule of a liquid is entirely contained inside the concave dissector and encased at the top by the flat upper side. To ease a breakage of the capsule upon a manual compression of the applicator through the upper side, to ensure the formulation stability and sufficient shelf life, and to save the packaging space, the capsule is formed as an easily peelable, high-barrier, and shallow blister. The blister may include an aid for its opening at a predetermined location. The blister can be composed of two opposing shells or of a bottom shell and a flat lid.

The upper side, dissector, and working side can be welded together along the edge of the applicator resulting in a rounded seam that essentially follows the spherical curvature of the dissector. In addition to its uniform thickness and seal strength, such a seam has an edge that does not scratch surfaces.

DETAILED DESCRIPTION OF THE INVENTION

The invention is a hand applicator of encapsulated liquids for their even distribution on surfaces. The applicator includes an upper side (an impermeable membrane), a capsule of a liquid, an evenly perforated dissector, and a working side (an absorber). The upper side, dissector, and working side are fixed together along the edge of the applicator. A slight manual compression of the applicator causes the capsule to open and release the liquid that flows through the dissector perforations and evenly infuses the absorber. The dissector of this invention is semi-rigid concave, which ensures an even application of the liquid on a variety of surfaces, particularly curved, and provides with a secure and essentially matching space to contain the entire capsule. The applicator is described in detail below.

Figure 1A:
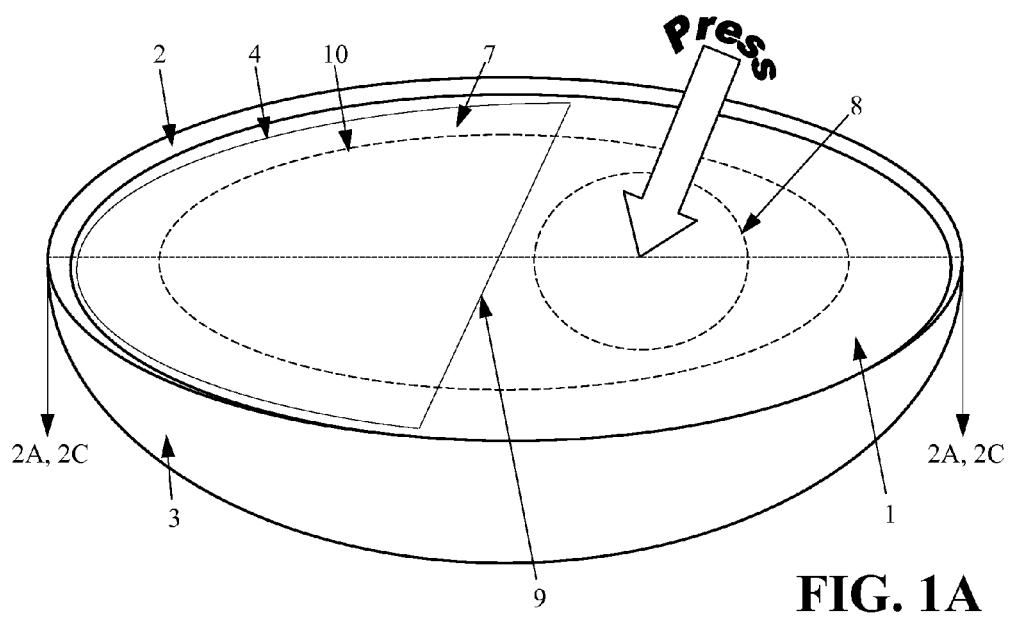
FIG. 1A is a front perspective view of the applicator of this invention in the storage position.

FIG. 1A is a front perspective view of the applicator of this invention in the storage position, which shows its upper side 1 with a welding seam 2 around the applicator, and a part of its working side 3. About a semicircular cut 4 is made through the upper side 1 (more precisely, through a semi-rigid membrane 5 and an outer membrane 6, FIG. 1B) along and close to the seam 2 to form a handle 7. A round aperture 8 in the semi-rigid membrane 5 is located centrally, close to the handle hinge 9, and projects onto a capsule 10 of a liquid 11 (FIG. 2A). A place for applying a manual pressure to open the capsule 10 is marked with an arrow "Press" and may correspond to the aperture 8 (if available).

The working side 3 composed of an absorber covers the outside of the dissector 12 and comes during an application in contact with the skin or other surfaces, particularly curved. The working side 3 is spherically rounded owing to the semispherical or semi-ellipsoid shape of the underlying semi-rigid dissector 12 (FIGS. 2A, 3A). The absorber is soft and produces pleasant tactile sensations, is rubbing-resistant, safe to the user, inert to the liquid 11, and capable of quickly absorbing and spreading the liquid 11 after its release out of the capsule 10. In a preferred embodiment, the absorber for the working side 3 is made of a woven napped textile (e.g., polyethylene terephthalate [PET] or cotton fleece) or of a polyurethane foam.

Figure 2A:
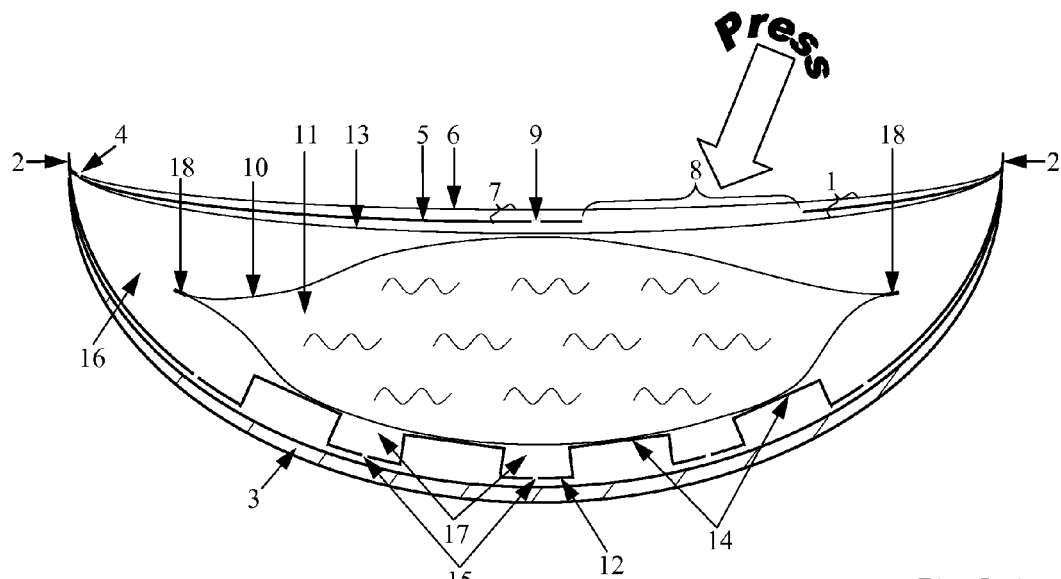
FIG. 2A is a front cross-sectional view of the applicator in the storage position taken along line 2A, 2C-2A, 2C in FIG. 1A.
Figure 2B:
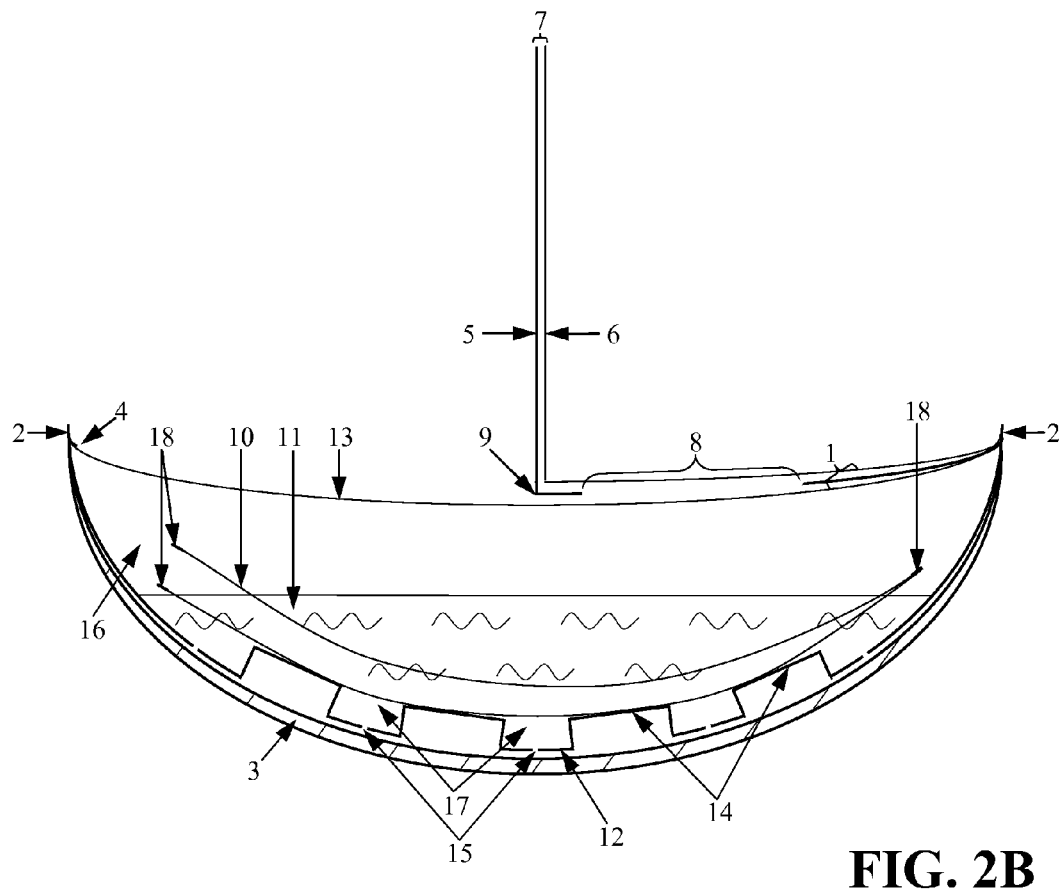
FIG. 2B is a front cross-sectional view of the applicator in the working position taken along line 2B, 2D-2B, 2D in FIG. 1B.
Figure 3A:
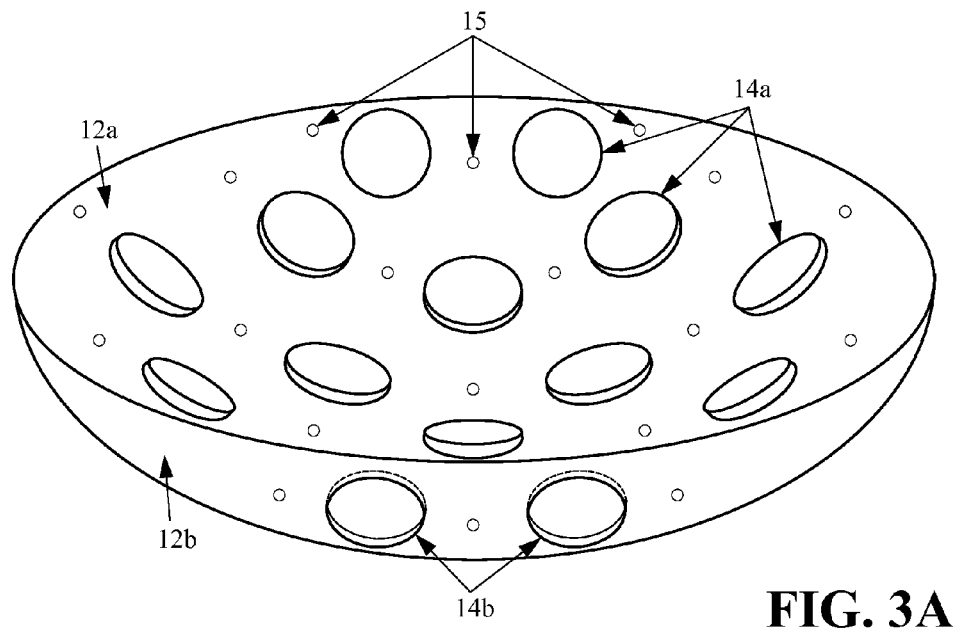
FIG. 3A is a front perspective view of the semi-rigid, concave, draining dissector.

FIG. 2A is a front cross-sectional view of the applicator in the storage position taken along line 2A, 2C-2A, 2C in FIG. 1A. The applicator includes—from the top to the bottom— the upper side 1 formed by overlying flat membranes (outer 6, semi-rigid 5, and impermeable 13), a capsule 10, a semi-rigid concave draining dissector 12, and the working side 3 composed of an absorber. The upper side 1, dissector 12, and working side 3 are fixed together (e.g., by welding or gluing) along the edge of the applicator. In a preferred embodiment, a spherically inward rounded seam 2 is produced to avoid scratching of the skin or other surfaces by the seam edge during an application. The semi-rigid concave dissector 12 ensures the stability of the applicator in use irrespective of the surface curvature (which is particularly important for the face and areas with soft and pliable underlying tissues) and application techniques (such as fast massaging or holding the applicator at an angle to the skin or other surfaces), and provides with a secure and approximately matching space to contain a fragile capsule 10 (in a preferred embodiment, an easily peelable blister). The concave dissector 12 includes essentially evenly spread elevations 14 on its inside and evenly spread perforations 15 dispersed between the elevations 14. The dissector 12 forms a cavity 16 for containing the entire capsule 10. The capsule 10 of a liquid 11 is encased between the concave dissector 12 and the flat impermeable membrane 13 at the top. A draining space 17 is created between elevations 14 where the released liquid 11 freely flows to reach the perforations 15 without being obstructed by the collapsed capsule or the user's fingers (FIG. 2B). The evenly spread perforations 15 evenly dissect the liquid squirt to achieve an even distribution of the released liquid 11 in the absorber of the working side 3, which together with the dissector 12 being semi-rigid concave, ensures an even application of the liquid from the absorber on a variety of surfaces, particularly non-flat. The cavity 16 and capsule 10 approximately match in geometry, so that the capsule 10 occupies a substantial portion of the cavity 16 and rests practically immobile between multiple, geometrically matching elevations 14 and the impermeable membrane 13.

The entire capsule 10 is contained within the dissector cavity 16 and does not extend beyond the edge of the dissector 12. As a result, the flat membranes (outer 6, semi-rigid 5, and impermeable 13) compose the flat upper side 1 of the applicator without folding over the capsule 10, which would otherwise compromise the quality (the uniform thickness and seal strength) of the seam 2. In the embodiment where the seam 2 follows the spherical curvature of the semi-rigid dissector 12, the upper side 1 is essentially flat (i.e. flat except for the area of the inward rounded seam 2, FIG. 2A). The outer surface of the upper side 1 (usually, the semi-rigid membrane 5 or the outer membrane 6) is printable to mark an area onto which the user should press, and to display product information (product name, direction for use, manufacturing or expiration date, batch number, etc).

In the prior art (Tereschouk) applicator, the dissector and the back side of the applicator were made of soft flexible materials. After a break of the capsule, the applicator was collapsing and losing its stability (the absorber was becoming flabby and folding; the grip was loose and poorly controllable). Upon use, the applicator was warping, and its front edge was often bending down, particularly, on a flabby, folding, or dry skin or when the applicator met body elevations or was used on other curved surfaces, or when rubbing movements were fast. The bent applicator could no longer be used.

In the prior art applicator, the capsule was elastically fixed between the flat flexible dissector and back side of the applicator, which were stretching over the capsule from the opposite sides. The stretched flexible materials produced folds (12 in FIG. 8 in Tereschouk) resulting in a varying thickness of the seam along the edge of the applicator, and thus in a non-uniform seal strength of the seam and potential leakages.

Though Tereschouk indicated that the dissector or the back side or both of them could be made sufficiently rigid to provide the applicator with warp-resistance in use, or that an additional element of rigidity to support the applicator could be used, no solution was offered. At the same time, for a normally functioning prior art applicator, it was critical to preserve its collapsibility (the applicator could be brought into the working position with an upright grip only after the capsule underneath had ruptured and the applicator had flattened) and the elasticity of the back side and dissector (the capsule was elastically compressed between them to prevent its dislodgment and also to increase its internal pressure).

In general, rigidity and flexibility (elasticity) are opposite, mutually excluding, qualities. Only the dissector, and to a much smaller degree, the back side of the prior art applicator could have been made less flexible (more rigid) without preventing the applicator from collapsing, or without the back side and dissector losing their compressive elasticity. In addition, more rigid flat dissector and back side would have aggravated the problem of their folding (more rigid materials cause coarser folding) and of the applicator seam leaking.

This invention solves the not identified in the prior art problems of the instability of the collapsed applicator and of the leakage of the applicator seam, and the identified in the prior art but unresolved problem of the applicator warping and bending in use, by creating a dissector 12 that is semi-rigid (to the extent of making the applicator non-collapsible and unbending) and concave (with an internal cavity 16 matching the capsule 10). The semi-rigid dissector 12 creates a semi-spherical support for the working side 3 smoothly gliding over body parts or other curved surfaces. As shown in FIG. 2A, the concave draining dissector 12 forms a cavity 16 for containing the entire capsule 10 and allows the flat membranes 6, 5, and 13 of the upper side 1 to be evenly overlaid over the dissector 12 and fixed (e.g., welded) along the edge of the applicator without folding. This ensures a uniform thickness, and thus, a uniform seal strength of the entire seam around the applicator.

When the soft-wall prior art applicators were stored in a stack one atop the other (e.g., in a packaging cylinder) to save the storage space, the capsules of the applicators at the bottom could spontaneously rupture under the weight of the applicators above. The semi-rigid concave dissector 12 of this invention protects the fragile capsule 10 in such a way that the applicators can be securely stacked when they face each other with the same side (the working side 3 of one applicator touching the working side 3 of an adjacent applicator, and the edge seam 2 of one applicator touching the edge seam 2 of an adjacent applicator).

The capsule of the prior art applicator was preferably pressurized and additionally elastically compressed between the flexible back side and dissector to further ease its rupture upon a manual compression. However, too rare, if any, materials provide both a low mechanical strength (allowing the capsule to be easily broken in the hand) and high barrier properties (allowing required stability and shelf life of liquid formulations).

Figure 3B:
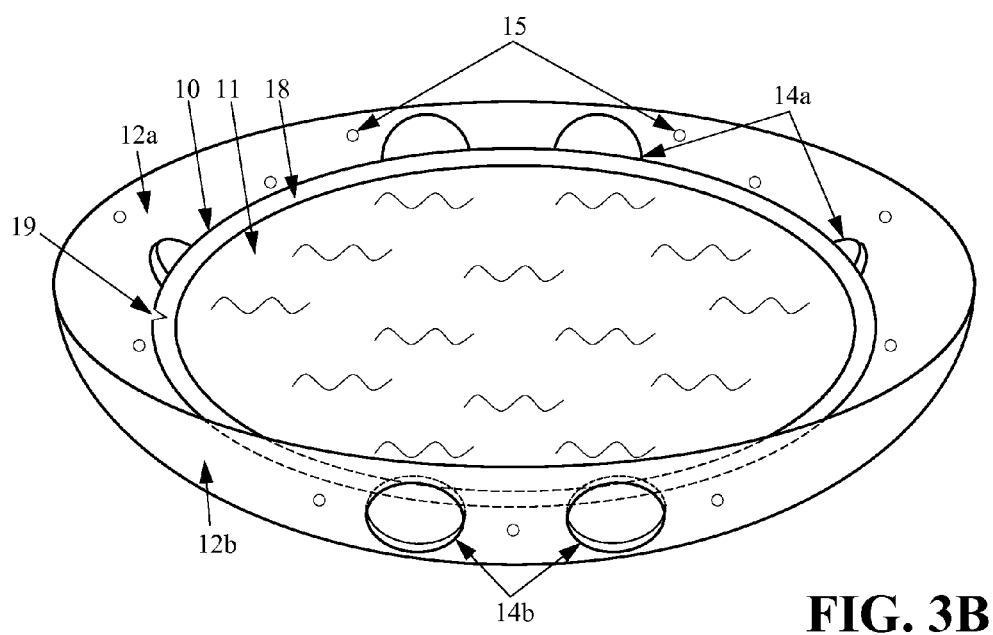
FIG. 3B is a front perspective view of the semi-rigid, concave, draining dissector containing a capsule.

In this invention, the capsule 10 is made of a material that is safe to the user, inert to the liquid 11, and high-barrier, and which easily opens upon a slight manual compression of the applicator. In a preferred embodiment, the capsule 10 is a rounded (spherical or ellipsoid), shallow (approximately matching the cavity 16 of the concave dissector 12) blister formed of an easily peelable (peel strength from below 1 to about 4 N per 15 mm) aluminum or high-barrier plastic coextruded films or laminates, which is filled with a liquid 11 under normal pressure and without gas (inert gas is preferable to air, if unavoidable), and sealed with a round seam 18 (FIG. 3B). The easily peelable material is a layer or a lacquer that is safe to the user, compatible with the liquid 11, and does not allow an undesirable outward migration of the liquid 11 ingredients. Such a shallow blister easily peels apart upon a slight manual compression, ensures sufficient stability and shelf life, and being about twice lower than the prior art pressurized capsule containing the same liquid volume, saves about half of the storage space. Blisters are produced as appropriate for the materials used, e.g., by cold forming of an aluminium foil and by thermoforming of plastics. There can be multiple capsules of different liquids within the same applicator.

In an embodiment shown in FIG. 2A, the capsule 10 is a blister composed of two opposing shells. In another embodiment, the capsule 10 can be a blister composed of a bottom shell and a flat lid. A blister with a flat lid may be fixed inside the dissector cavity 16 tighter thanks to a better matching geometry, but would require a deeper forming than a blister composed of two opposing shells to achieve the same volume.

In the prior art applicator, the volume of the cavity surrounding the capsule considerably exceeded the volume of the capsule itself to quickly dampen down the high pressure at which the liquid was released from a ruptured capsule. In this invention, the easily openable capsule (easily peelable blister) 10 opens (peels apart at the seam 18) at a low pressure and does not require much of the surrounding volume to reduce the pressure, but only as little of the volume as is needed for the released liquid to freely reach the unobstructed space 17 in the draining dissector 12. This allows an about matching geometry of the dissector cavity 16 and the shallow capsule 10 and further contributes to the reduction of the applicator size.

The absorber, dissector, and back side of the prior art applicator were assembled together by welding along the edge of the applicator, which produced a seam that was parallel to the working surface of the applicator. The stiff seam edge could scratch the skin when the applicator bent or met body elevations (e.g., nose, upper parts of the orbit, ear, and armpit walls). In the applicator of the present invention, the seam 2 (which includes welded edges of the outer membrane 6, semi-rigid membrane 5, impermeable membrane 13, dissector 12, and absorber of the working side 3) is spherically rounded inward (approximates the semispherical shape of the concave dissector 12), so that only the soft working side 3 (but not the stiff edge of the seam 2) contacts the skin during an application. In addition, the spherically rounded welding seam 2 makes the edge of the applicator much suppler upon a side impact on body parts than the edge of a welding seam that is parallel to the working surface, and thus makes the applicator use more pleasant.

Figure 1B:
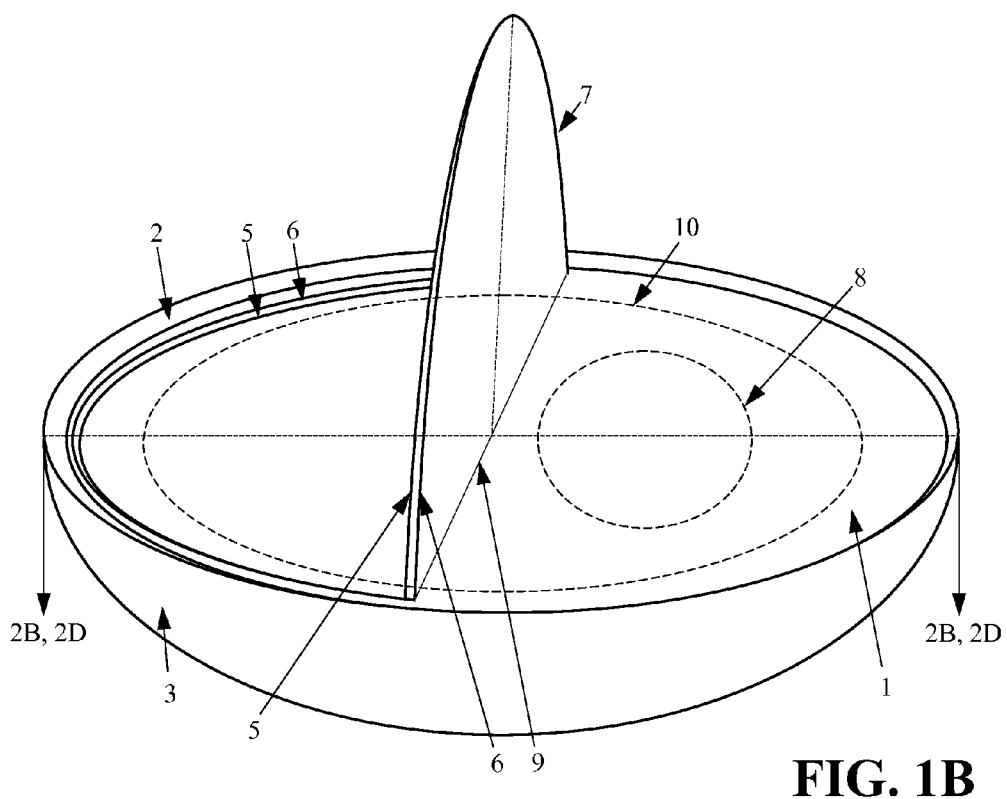
FIG. 1B is a front perspective view of the applicator of this invention in the working position.
Figure 1C:
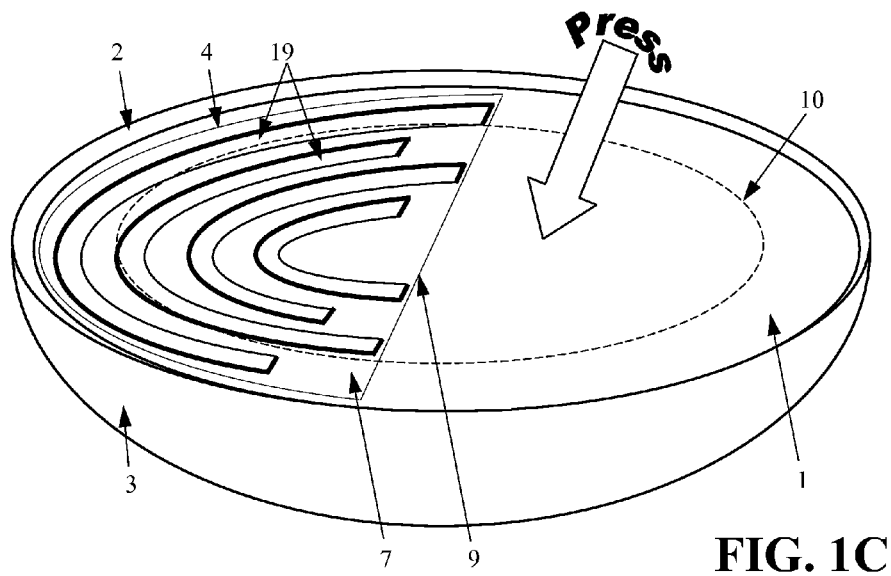
FIG. 1C is a front perspective view of the applicator in the storage position showing a handle with stiffeners.
Figure 1D:
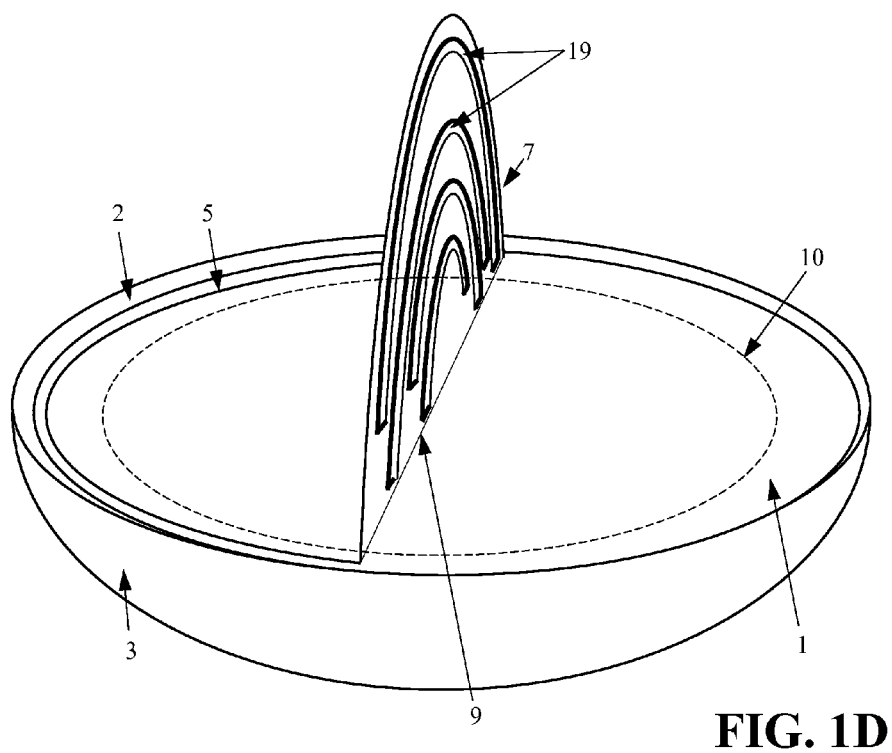
FIG. 1D is a front perspective view of the applicator in the working position showing a handle with stiffeners.

FIG. 1B is a front perspective view of the applicator of this invention in the working position, after the capsule 10 has opened and flattened, and the handle 7 risen in the working vertical position. The handle 7 is a semi-circular cut-through portion (a flap) of the semi-rigid membrane 5 (and the outer membrane 6, when available). A hinge 9 at the base of the handle 7 is made as a superficial (not full) cut, line perforations, or another type of a joint. Preferably, the hinge 9 is located at the diameter of the applicator and divides the upper side 1 in halves, which ensures the balance holding the applicator by the handle 7 and contributes to the even application of liquids on surfaces (FIGS. 1B, 1D). Pressing with a finger on the fixed portion of the semi-rigid membrane 5 (on its right part in FIG. 1B) slightly raises the handle 7 as a lever around the hinge 9. Then, the raised handle 7 can be easily grasped by fingers and brought further up into the working vertical position. The semi-rigid membrane 5 may have an aperture 8 (of about 15 mm in diameter) in its fixed portion over the capsule 10, through which the user's finger presses directly onto the capsule 10 (through a thin impermeable membrane 13), which further contributes to the easiness of the capsule 10 opening (FIGS. 2A, 2B). The aperture 8 may be concealed from outside by a thin outer membrane 6, which also improves printing, tactile, and optical characteristics of the applicator. The outer membrane 6 is made of a thin, flexible, printable, and usually non-transparent (unless it is desirable to show the color of the liquid 11) film (e.g., a flocked PET sheet).

Comparing FIG. 1A with FIG. 1B, it is seen that the applicator has not collapsed (as would have been expected from the prior art), but preserved its original rounded semi-spherical shape owing to the concave dissector 12, which serves a semi-rigid skeleton for the applicator and contributes to the stability of the handle 7 formed from the semi-rigid membrane 5 (FIGS. 2A, 2B).

In the prior art applicator, the grip (7 in FIG. 8 in Tereschouk) formed by a duplication of the back side increased the thickness of the welded back side at its ends by 3 times. This aggravated the problem of the non-uniform seam thickness and seal strength that was caused by the flexible flat sheets (back side and dissector) folding over the capsule and resulted in the applicator seam leakage. The handle 7 of the applicator of the present invention is formed by a semi-circular cut 4 through the flat semi-rigid membrane 5 (and outer membrane 6, when available), which contributes to the uniform thickness and seal strength of the applicator seam 2.

The semi-rigid membrane 5 contributes to the stability of the applicator created primarily by the semi-rigid dissector 12, and provides with stable structure and support to the cut-through handle 7. A material used for the semi-rigid membrane 5 (and the handle 7 as its cut-through portion) should be able to resiliently bend down to enable a breakage of the capsule 10 upon a slight compression of the applicator (unless an aperture 8 is provided to ease the capsule 10 opening). The semi-rigid membrane 5 can be made of a semi-rigid thermoplastic (e.g., polyolefin or PET) sheet that could be equally or less rigid (thinner) than the one used for the semi-rigid dissector 12.

To improve the stability of the cut-through handle 7 and to prevent its bending back and forth in the user's fingers during an application, the handle 7 is provided with stiffness ribs (stiffeners) 19. FIGS. 1C and 1D are front perspective views of the applicator showing a handle 7 with stiffeners 19 in the storage and working positions, respectively. In a preferred embodiment, a sheet for the semi-rigid membrane 5 and handle 7 with stiffeners 19 is produced by thermoplastic molding or thermoforming. Stiffeners extending in different directions (e.g., semicircular as shown in FIGS. 1C and 1D) ensure the handle 7 stability irrespective of the manner holding the handle 7 or the direction of the massaging movements.

FIG. 2B is a front cross-sectional view of the applicator in the working position taken along line 2B, 2D-2B, 2D in FIG. 1B. Upon a manual compression of the applicator by the user, the seam 18 on the left of the capsule 10 separates (the easily peelable blister peels apart), the liquid 11 leaks out of the capsule 10 into the cavity 16 of the concave dissector 12, and freely (being unblocked by the torn flattened capsule 10, which rests on elevations 14 of the dissector 12) flows in the unobstructed draining space 17 between elevations 14 and then through perforations 15 to the working side 3. The dissector 12 depicted in FIG. 2B is draining in the sense that it both drains (collects) the released liquid 11 in the unobstructed space 17 and evenly dissects (divides) the liquid squirt into trickles by evenly spaced perforations 15.

The impermeable membrane 13 prevents a contact between the user's hand and the liquid 11 released out of the capsule 10. It is made of a safe to the user, inert to the liquid, thin, flexible impermeable, non-absorbing film (e.g., a PET sheet), which may be transparent to show the color of the liquid 11 or not.

Figure 2C:
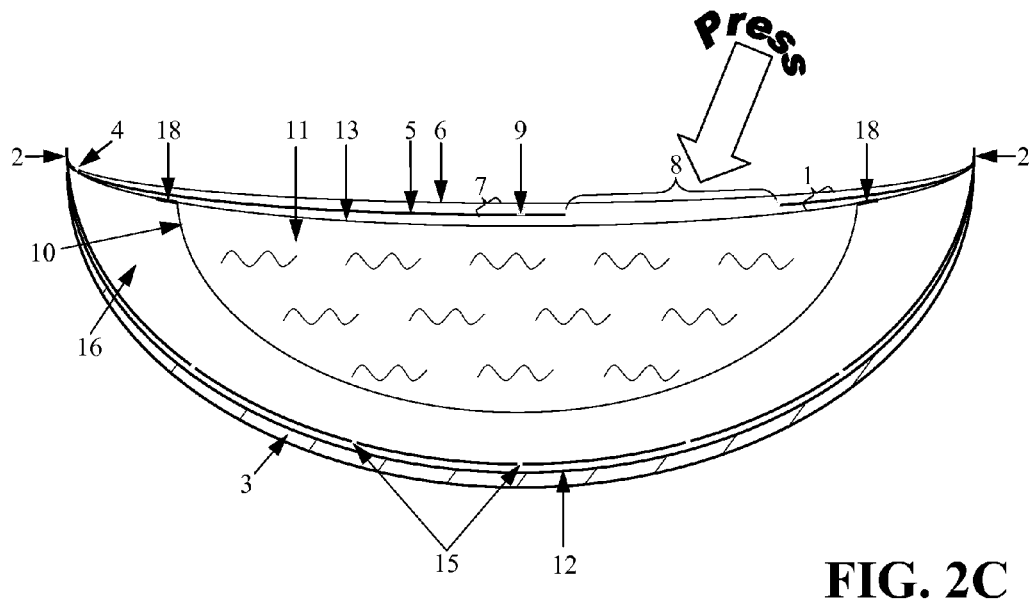
FIG. 2C is a front cross-sectional view of the applicator in the storage position taken along line 2A, 2C-2A, 2C in FIG. 1A and showing the capsule and impermeable membrane with a common wall.
Figure 2D:
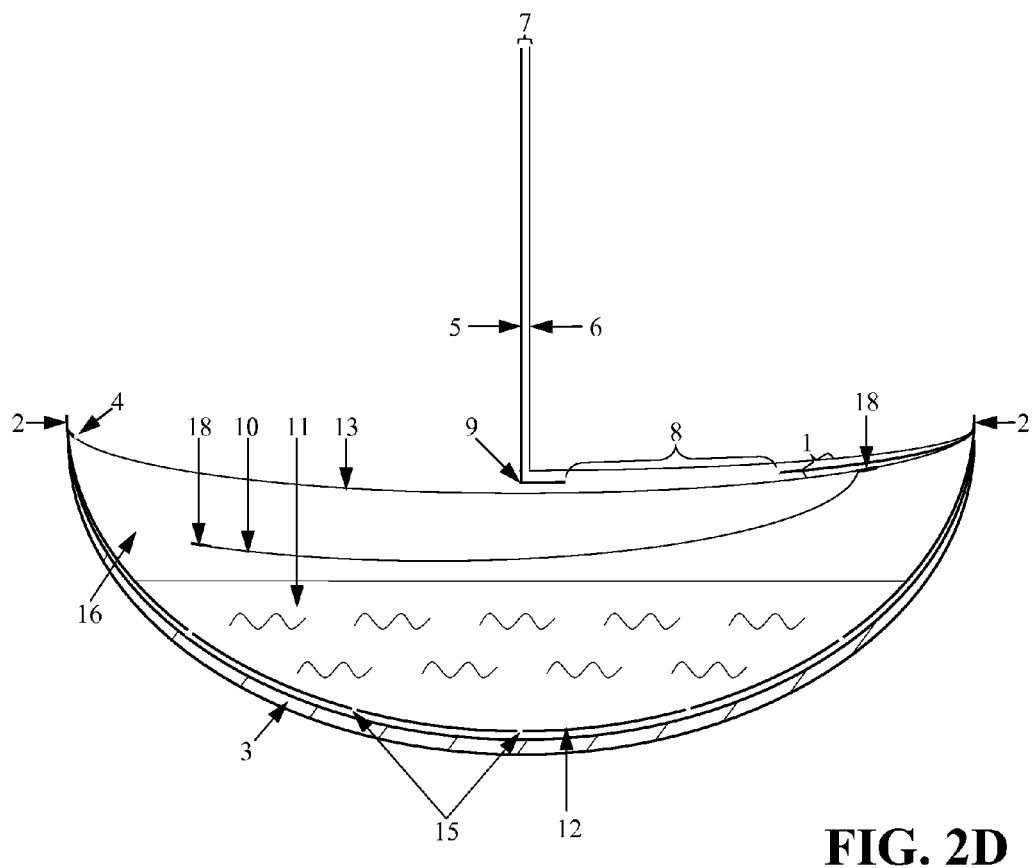
FIG. 2D is a front cross-sectional view of the applicator in the working position taken along line 2B, 2D-2B, 2D in FIG. 1B and showing the capsule and impermeable membrane with a common wall.

FIG. 2C is a front cross-sectional view of the applicator in the storage position taken along line 2A, 2C-2A, 2C in FIG. 1A and showing the capsule 10 and impermeable membrane 13 with a common wall (the impermeable membrane 13 forms the upper wall of the capsule 10). FIG. 2D is a front cross-sectional view of the applicator in the working position taken along line 2B, 2D-2B, 2D in FIG. 1B and showing the capsule 10 and impermeable membrane 13 with a common wall. This embodiment ensures a firm permanent fixation of the capsule 10 inside (and, for a single capsule, preferably, at the center of) the dissector cavity 16 and saves materials and production steps. The capsule 10 does not touch the dissector 12 and thus does not close perforations 15 (FIG. 2D), which obviates the need for elevations on the dissector 12 inside. This embodiment also eliminates the idle space between the impermeable membrane 13 and the opened capsule 10 where some released liquid 11 would otherwise rest and be wasted (FIG. 2D). Alternatively, the impermeable membrane 13 and capsule 10 can be fixed together (e.g., glued) without forming a common wall.

FIG. 3A is a front perspective view of the semi-rigid, concave (semi-spherical or semi-ellipsoid), draining dissector 12, which includes evenly spaced perforations 15 interspersed between evenly spread elevations 14. The elevations 14 on the inner concave surface of the dissector 12 create a geometrically matching support for the spherical capsule 10 (FIG. 3B), evenly distribute the capsule 10 weight over numerous elevations 14, and form an unobstructed draining space for the liquid 11 released out of the capsule 10. The geometrically matching elevations 14 determine the lower boundary of the dissector cavity 16, which provides with a secure and essentially matching space to contain the entire capsule 10 (FIGS. 2A, 3B). In a preferred embodiment, the concave dissector 12 and elevations 14 are produced by thermoforming a plastic sheet into a blister, the inner surface 12a of which exhibits elevations (knobs) 14a and the outer surface 12b shows mirroring depressions (pits) 14b. Other types of plastic processing (e.g., injection molding and other types of molding) can be used as well. The semi-rigid concave draining dissector 12 is made of a safe to the user, inert to the liquid 11, semi-rigid, non-absorbing material (e.g., a thermoplastic sheet of 0.1-0.5 mm polyolefin or PET).

FIG. 3B is a front perspective view of the semi-rigid, concave, draining dissector 12 containing the entire, geometrically matching capsule (shallow blister) 10, which rests on elevations 14 without closing perforations 15 and does not extend beyond the edge of the concave dissector 12. An aid for the capsule 10 opening at a predetermined location, such as a marginal cut 19 of the seam 18 or a short segment of the seam 18 with a lower seal strength, may be used to determine the desired location of an opening in the capsule 10. This could be used to indicate to the user that the capsule 10 has opened and show the released liquid 11 through a transparent impermeable membrane 13.

Although only a limited number of specific embodiments have been described in detail, such description is not to be taken as a limitation of the present invention. The description has been given only as illustration and example. To those skilled in the art, it will be readily apparent that changes may be made without departing from the spirit of the disclosed inventive concepts. The scope of the invention is to be defined by the appended claims.

I claim:

1. A hand applicator of encapsulated liquids for their even distribution on surfaces, said applicator including an upper side, a capsule of a liquid, an evenly perforated dissector, and a working side, wherein: said upper side includes an impermeable membrane; said capsule is placed between said impermeable membrane and said dissector; said working side covers the outside of said dissector; said upper side, dissector, and working side are fixed together along the edge of said applicator; and whereby a manual compression of said applicator causes said capsule to open and release said liquid, which flows through said dissector and evenly infuses said working side; characterized in that said dissector is non-collapsible semi-rigid concave and contains said capsule.

2. The applicator of claim 1 wherein said upper side includes a semi-rigid membrane outside said impermeable membrane.

3. The applicator of claim 1 wherein said upper side is flat and non-folding.

4. The applicator of claim 1 wherein said dissector has elevations on its inside that geometrically match said capsule and create an unobstructed draining space for said released liquid.

5. The applicator of claim 1 wherein said impermeable membrane and said capsule are permanently fixed together.

6. The applicator of claim 1 wherein said impermeable membrane and said capsule have a common wall.

7. The applicator of claim 1 wherein said capsule is a blister.

8. The applicator of claim 1 wherein said capsule is high-barrier.

9. The applicator of claim 1 wherein said capsule is easily peelable.

10. The applicator of claim 1 wherein said capsule includes an aid for its opening at a predetermined location.

11. The applicator of claim 1 wherein said upper side, dissector, and working side are welded together along the edge of said applicator resulting in a rounded seam that essentially follows the spherical curvature of said dissector.

12. The applicator of claim 2 wherein said upper side includes an outer membrane outside said semi-rigid membrane.

13. A hand applicator of encapsulated liquids for their even distribution on surfaces, said applicator including an upper side, a capsule of a liquid, an evenly perforated dissector, and a working side, wherein: said upper side includes an impermeable membrane; said capsule is placed between said impermeable membrane and said dissector; said working side covers the outside of said dissector; said upper side, dissector, and working side are fixed together along the edge of said applicator; and whereby a manual compression of said applicator causes said capsule to open and release said liquid, which flows through said dissector and evenly infuses said working side; characterized in that said dissector is semi-rigid concave and contains said capsule, said upper side includes a semi-rigid membrane outside said impermeable membrane, and said semi-rigid membrane has an aperture over said capsule.

14. The applicator of claim 2 wherein said semi-rigid membrane has a cut-through handle.

15. The applicator of claim 4 wherein said dissector is produced by thermoforming or molding.

16. The applicator of claim 7 wherein said blister is composed of two opposing shells or of a bottom shell and a flat lid.

17. A hand applicator of encapsulated liquids for their even distribution on surfaces, said applicator including an upper side, a capsule of a liquid, an evenly perforated dissector, and a working side, wherein: said upper side includes an impermeable membrane; said capsule is placed between said impermeable membrane and said dissector; said working side covers the outside of said dissector; said upper side, dissector, and working side are fixed together along the edge of said applicator; and whereby a manual compression of said applicator causes said capsule to open and release said liquid, which flows through said dissector and evenly infuses said working side; characterized in that said dissector is semi-rigid concave and contains said capsule, said upper side includes a semi-rigid membrane outside said impermeable membrane, wherein said semi-rigid membrane has a cut-through handle including a hinge at the base of said handle.

18. A hand applicator of encapsulated liquids for their even distribution on surfaces, said applicator including an upper side, a capsule of a liquid, an evenly perforated dissector, and a working side, wherein: said upper side includes an impermeable membrane; said capsule is placed between said impermeable membrane and said dissector; said working side covers the outside of said dissector; said upper side, dissector, and working side are fixed together along the edge of said applicator; and whereby a manual compression of said applicator causes said capsule to open and release said liquid, which flows through said dissector and evenly infuses said working side; characterized in that said dissector is semi-rigid concave and contains said capsule, said upper side includes a semi-rigid membrane outside said impermeable membrane, wherein said semi-rigid membrane has a cut-through handle, wherein said handle includes stiffeners.

19. The applicator of claim 17 wherein said hinge is located at the diameter of said applicator.

20. The applicator of claim 18 wherein said semi-rigid membrane is produced by thermoforming or molding.

* * * * *